(12) United States Patent
Tearney et al.

(10) Patent No.: US 6,341,036 B1
(45) Date of Patent: Jan. 22, 2002

(54) CONFOCAL MICROSCOPY WITH MULTI-SPECTRAL ENCODING

(75) Inventors: Guillermo J. Tearney, Cambridge; Brett E. Bouma, Quincy; Robert H. Webb, Lincoln, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/622,971

(22) PCT Filed: Feb. 26, 1999

(86) PCT No.: PCT/US99/04356

§ 371 Date: Aug. 24, 2000

§ 102(e) Date: Aug. 24, 2000

(87) PCT Pub. No.: WO99/44089

PCT Pub. Date: Sep. 2, 1999

Related U.S. Application Data
(60) Provisional application No. 60/076,041, filed on Feb. 26, 1998.

(51) Int. Cl.[7] ............................................. G02B 21/00
(52) U.S. Cl. ...................................... 359/368; 359/209
(58) Field of Search ................................ 359/368, 389, 359/196, 209, 385

(56) References Cited

U.S. PATENT DOCUMENTS

| | | | |
|---|---|---|---|
| 4,965,441 A | 10/1990 | Picard | |
| 5,127,730 A | 7/1992 | Brelje et al. | |
| 5,248,876 A | 9/1993 | Kerstens et al. | |
| 5,304,810 A | 4/1994 | Amos | |
| 5,450,203 A | 9/1995 | Penkethman | |
| 5,459,325 A | 10/1995 | Hueton et al. | |
| 5,526,338 A | 6/1996 | Hasman et al. | |
| 5,565,986 A | 10/1996 | Knuttel | |
| 5,600,486 A | 2/1997 | Gal et al. | |
| 5,698,397 A | 12/1997 | Zarling et al. | |
| 5,785,651 A * | 7/1998 | Kuhn et al. | 600/310 |
| 5,887,009 A * | 3/1999 | Mandella et al. | 372/6 |
| 6,111,645 A * | 8/2000 | Tearney et al. | 356/354 |

* cited by examiner

*Primary Examiner*—Cassandra Spyrou
*Assistant Examiner*—Mark A. Robinson
(74) *Attorney, Agent, or Firm*—FrommerLawrence&Haug LLP; Thomas J. Kowalski; Amy Leahy

(57) ABSTRACT

A scanning confocal microscopy system, especially useful for endoscopy with a flexible probe which is connected to the end of an optical fiber(9). The probe has a grating(12) and a lens(14) which delivers a beam of multi-spectral light having spectral components which extend in one dimension across a region of an object and which is moved to scan in another dimension. The reflected confocal spectrum is measured to provide an image of the region.

32 Claims, 7 Drawing Sheets

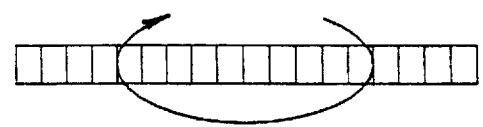
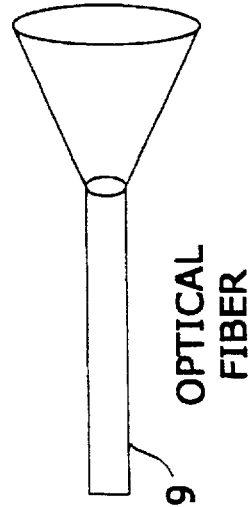
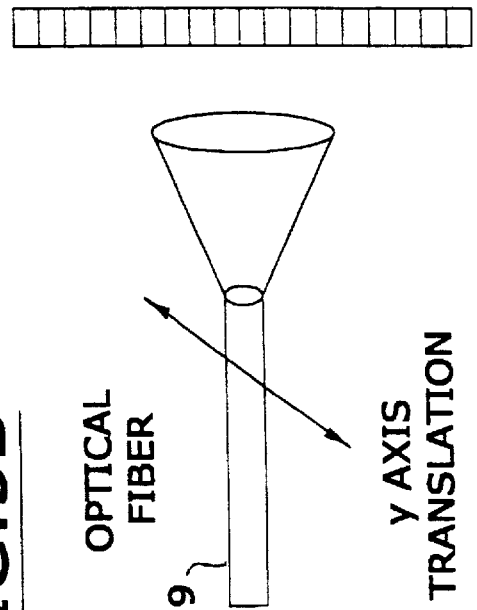
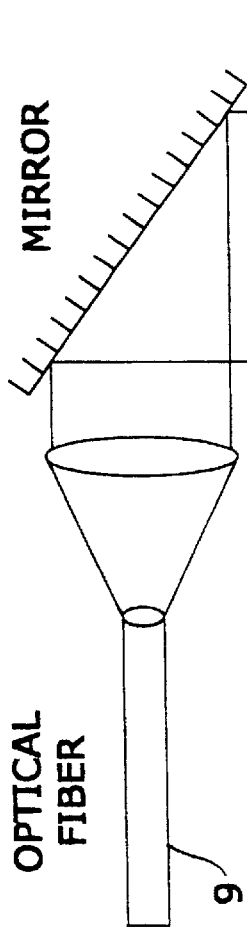
FIG. 5B
FIG. 5C
FIG. 5D

CONFOCAL MICROSCOPY WITH MULTI-SPECTRAL ENCODING

This application is a 371 of PCT/US99/04356 filed Feb. 26, 1999 which claims the priority benefit of U.S. Provisional Application No. 60/076,041, filed Feb. 26, 1998.

DESCRIPTION

The present invention relates to systems (method and apparatus) for confocal microscopy for the examination or imaging of sections of a specimen of biological tissue, and particularly to such systems using multi-spectral illumination and processing of multi-spectral light.

Currently, the use of fast scanning confocal microscopy is limited to accessible surfaces of the skin and the eye. The reason for this is that the only reliable methods for optical scanning must be performed in free space. In addition, the size of these optical scanners prohibit their use in small probes such as endoscopes or catheters. It is a feature of the invention to miniaturize the fast scanning mechanism and increase the number of medical applications of confocal microscopy to include all surfaces of the body, gynecologic applications, probe-based applications, and internal organ systems.

Multi-spectral light was proposed for use in confocal microscopy, but only for imaging vertically-spaced regions of a body under examination. See B. Picard, U.S. Pat. No. 4,965,441, issued Oct. 25, 1990. An interferometer using a grating to obtain multi-spectral light which is resolved in the interferometer to obtain a spectroscopic image is disclosed in A. Knuttal, U.S. Pat. No. 5,565,986, issued Oct. 15, 1996. A lens having a color separation grating which obtains a multi-spectral light is disclosed in U.S. Pat. No. 5,600,486, issued Feb. 4, 1997. Such multi-spectral proposals are not effective for high resolution imaging using a compact, flexible probe. A confocal microscope system according to this invention can be miniaturized and incorporated into a compact probe. In addition, by allowing light delivery through a single optical fiber, the probe may also be easily incorporated into catheters or endoscopes. Thus, a confocal microscope in accordance with the invention allows imaging of all accessible surfaces of the body and increases the biomedical applications of confocal microscopy by an order of magnitude.

Briefly described, a confocal microscopy system embodying the invention illuminates a region of interest in a body into which said probe may be inserted with a confocal spectrum extending along one dimension. Optics in said probe or physical movement of said probe enabled by attachment thereto of a flexible light conductive member (which may be an optical fiber), enables scanning of said spectrum along one or two additional dimensions thereby providing for two or three dimensional imaging of the region. The reflected confocal spectrum may be detected or decoded spectroscopically, preferably with a heterodyne detection mechanism which may be implemented interferometrically.

The invention will be more apparent from the following drawings wherein

FIG. 5A–D are schematic diagrams showing: (a) image formation; (b) translation of the optical fiber in the y direction; (c) rotation of the optical fiber in the forward firing mode; and (d) rotation of the optical fiber in the side firing mode.

Figure 6:
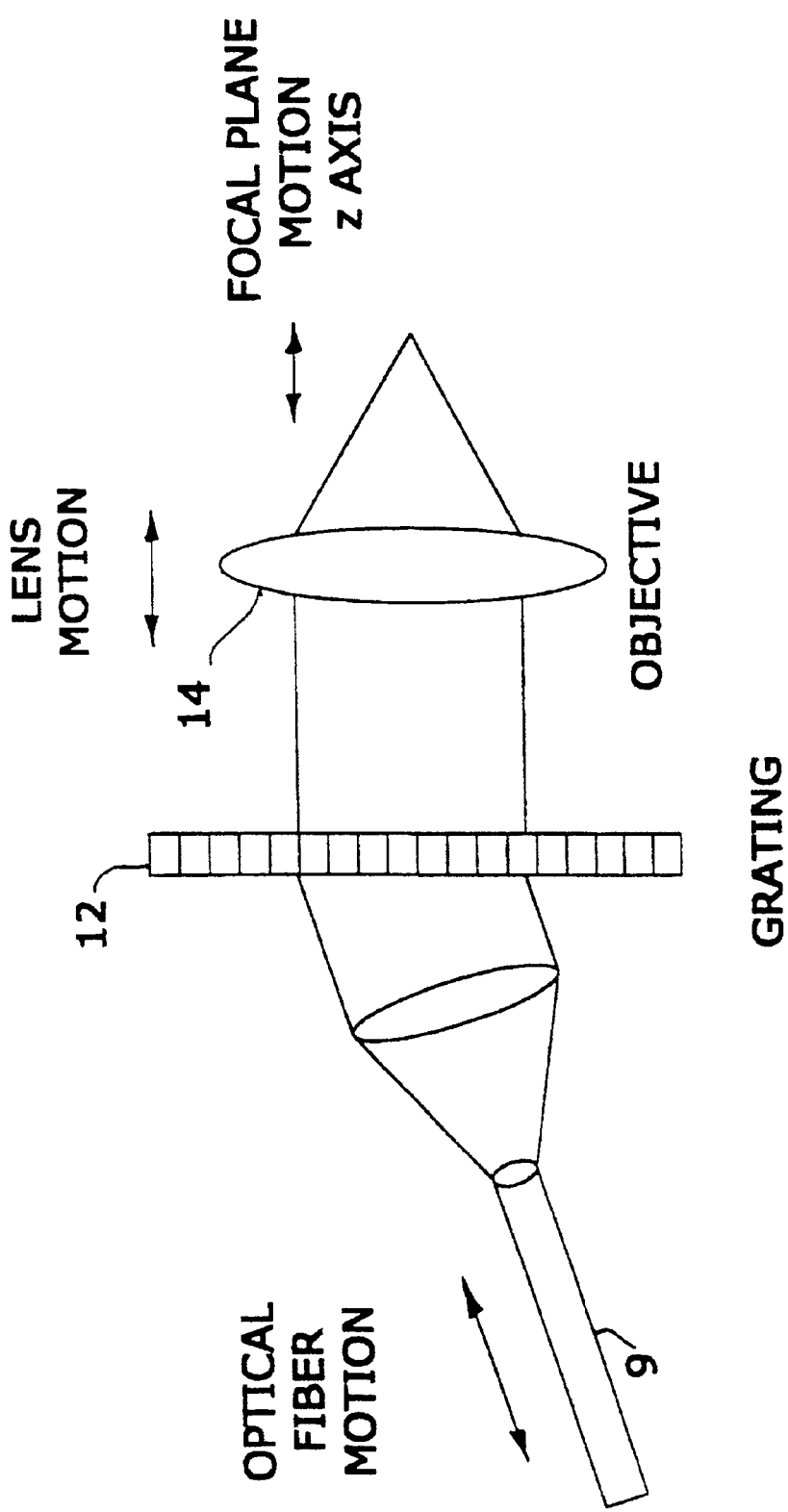

FIG. 6 is a schematic diagram showing cross-sectional image formation by scanning the optical fiber or the objective lens along the z axis using a system embodying the invention.

Figure 7:
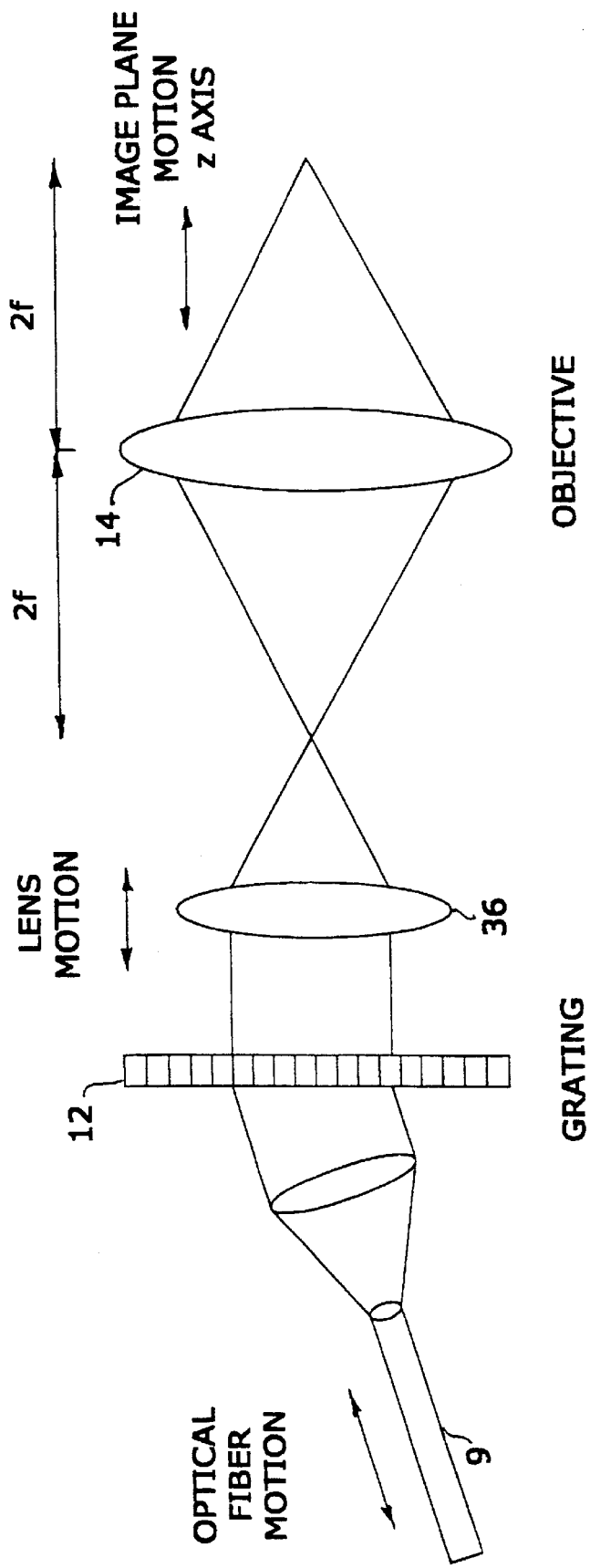

FIG. 7 is another schematic diagram of a system embodying the invention wherein optical zoom is achieved by moving the focus of an intermediate lens in and out of the image plan of the objective.

Figure 1:
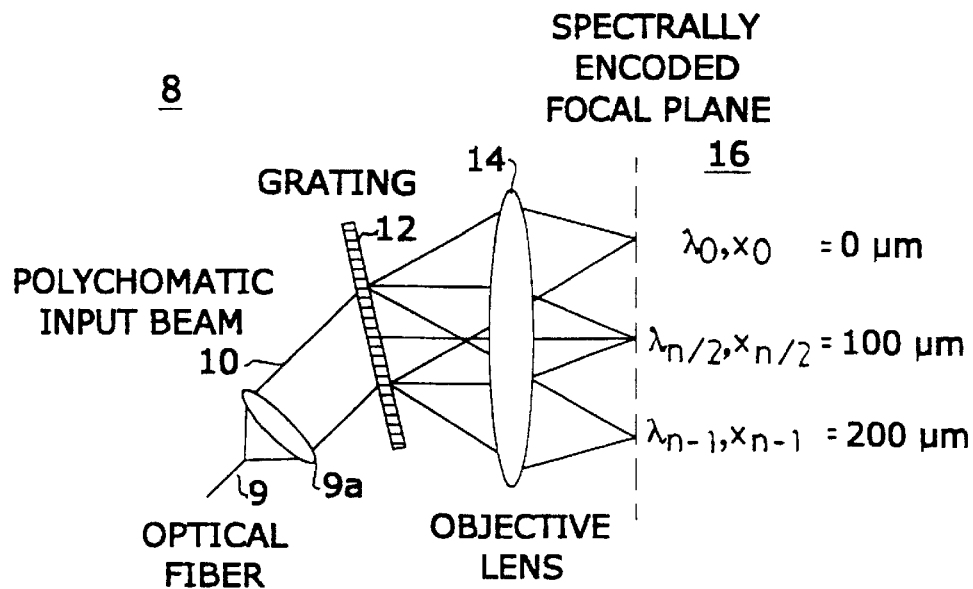
FIG. 1 is a schematic diagram of a spectrally encoded confocal probe in accordance with the invention where specific wavelengths are shown for illustrative purposes, their exact values depending on the optical parameters of the system.

Referring now to the figures, multi-spectral encoding for confocal microscopy uses a broad bandwidth source 10 as the input to the microscope. In the probe 8 of the microscope, the source spectrum provided via an optical fiber 9 is dispersed by a grating 12 and focused by an objective lens 14 onto the sample 16. A lens 9a is preferably disposed between the optical fiber 9 and the grating 12 to collimate the light from the optical fiber, as shown in FIG. 1, however, lens 9a may be removed. The spot for each wavelength is focused at a separate position, x, on the sample (FIG. 1). The reflectance as a function of transverse location is determined by measuring the reflected confocal spectrum from the sample 16 returned from probe 8.

The number of wavelengths or points that may be resolved is determined by:

$$\frac{\lambda}{\delta\lambda} = mN, \quad (1)$$

where $\lambda$ is the center wavelength, $\delta\lambda$ is the bandwidth of the spectrum, N is the number of lines in the grating 12 illuminated by the polychromatic input beam 10, and m is the diffraction order. If the total bandwidth of the source is $\Delta\lambda$, the number of resolvable points, n is defined by:

$$n = \frac{\Delta\lambda}{\delta\lambda} \quad (2)$$

Figure 2:
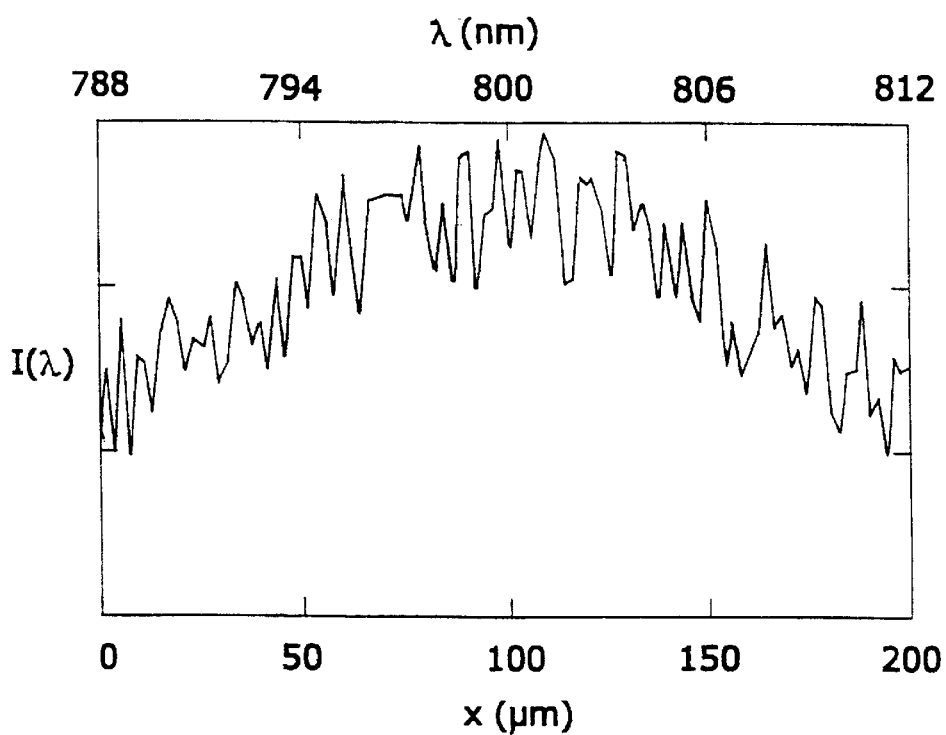
FIG. 2 is a plot of spectrally encoded light obtained by confocal detection using direct spectral detection in accordance with this invention, where different wavelengths are detected by turning the spectrometer grating.

For an input source with a center wavelength of 800 nm, a bandwidth of 25 nm, an input spot diameter of 5 mm, a diffraction grating of 1800 lines/mm and a diffraction order of 1, n=281 points may be resolved by the spectrally encoded confocal system (FIG. 2). The parameters used in this example may be found in common, inexpensive optical components. The number of points may be increased by simply increasing the input spot diameter or the bandwidth of the source. Increasing the spot diameter increases the resultant probe diameter. Increasing the bandwidth of the source could be accomplished by using a broader bandwidth superluminescent diode, a rare earth doped fiber superfluorescent source, or a solid state modelocked laser.

Figure 3:
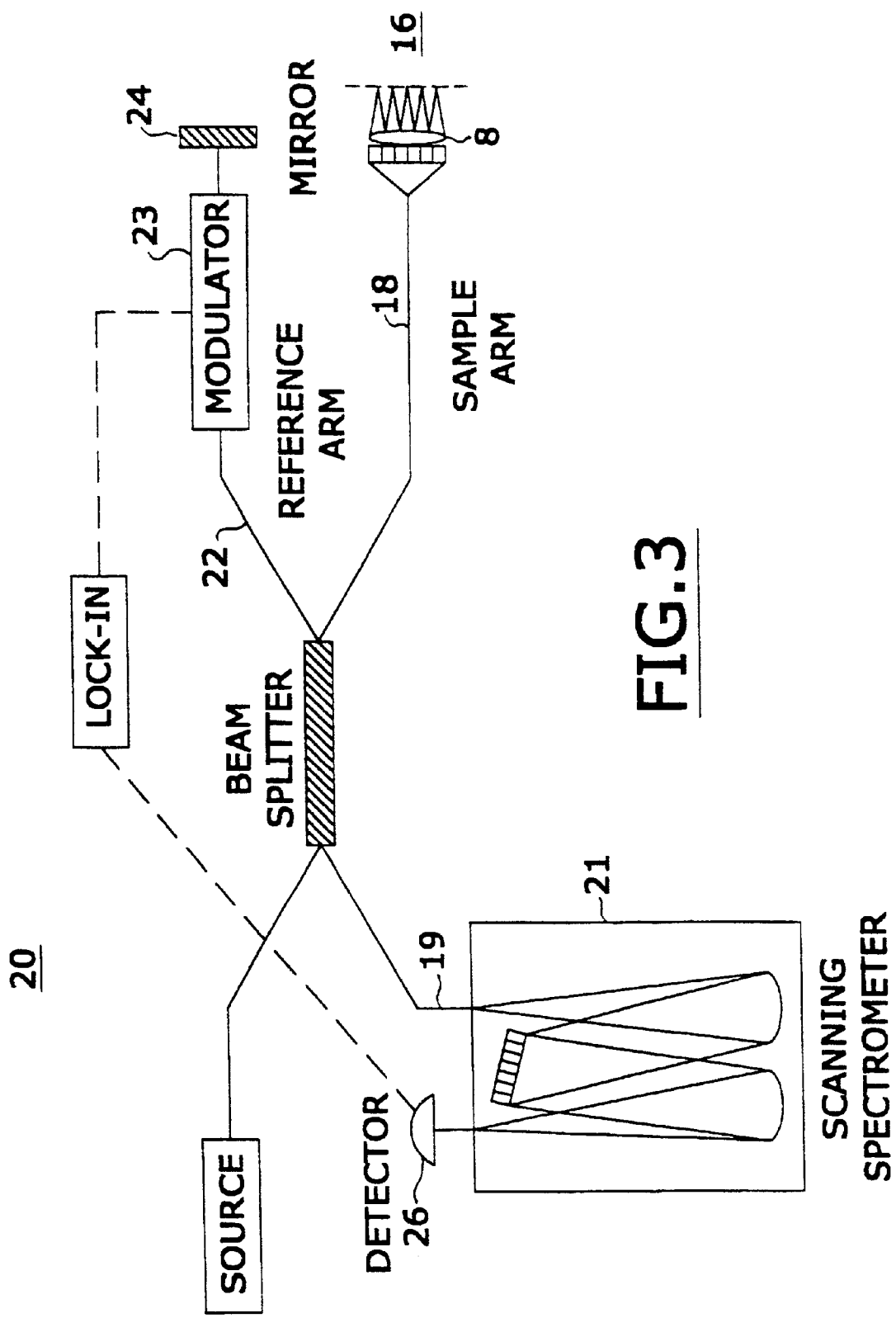
FIG. 3 is a schematic diagram showing a system embodying the invention using a spectrometer for measurement of the spectrum, $I(\lambda)$, which corresponds to reflectance from different transverse locations, x, on the specimen.

Consider next the multi-spectral process. First, consider direct spectral measurement. The reflectance from the sample 16 as a function of transverse location is determined by measuring the reflected confocal spectrum from the sample arm 18. The spectrum may be measured efficiently by incorporating the probe 8 in the sample arm of a Michelson interferometer 20 (FIG. 3) and detecting the light transmitted through a high resolution spectrometer 21 at the output port 19 of the interferometer. Thus, each wavelength measured corresponds to a separate position, x, on the sample (FIG. 3). The advantage to this method over traditional real time confocal microscopy is that the fast axis scanning (~15 kHz) may be performed external to the probe 8 by the spectrometer 21 with approximately 0.1 nm spectral resolution for the parameters given above, well within reach of high quality spectrometers.

High sensitivity may be achieved through the use of the heterodyne detection. If the reference arm 22 is modulated, such as by modulator 23 with mirror 24 (FIG. 3), the interference of light from the sample arm 18 and the reference arm 22 will also be modulated. High signal-to-noise ratios may be then achieved by lock-in detection on the reference arm modulation frequency of detector 26.

Figure 4:
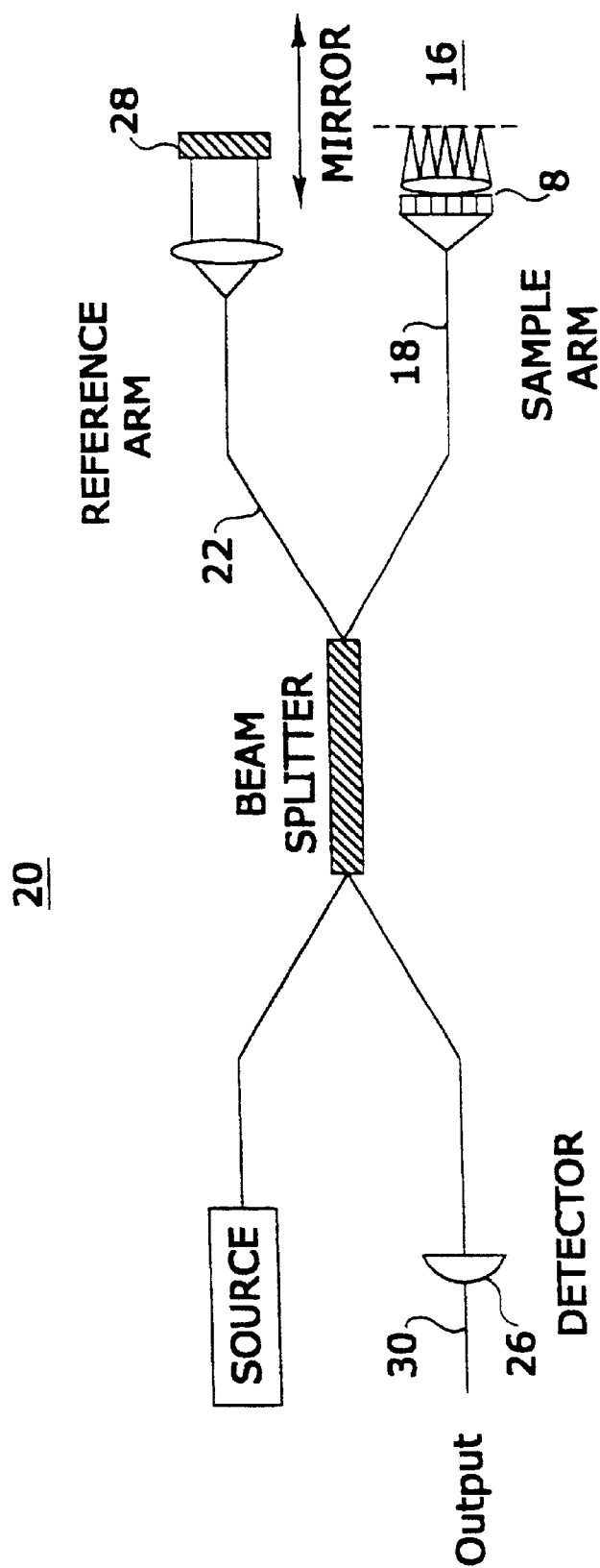
FIG. 4 is a schematic diagram of a system embodying the invention having spectrally encoded confocal detection using interference spectroscopy.

Another method for measuring the spectrum is interference or Fourier transform spectroscopy. This may be accomplished by inserting a linearly translating mirror 28 in the reference arm 22 and measuring the cross-correlation output 30 from the interference spectrometer due to the interference of the reflected light from the sample and reference arms 18 and 22, respectively (FIG. 4). The advantages to this type of spectroscopic detection include the ability to achieve higher spectral resolutions than direct detection methods, efficient use of the returned light, inherent modulation of the reference arm 22 by the Doppler shift of the moving mirror 28, and the capability to extract both reflectance and phase data from the sample 16. The ability to extract phase data from the sample may allow detection of refractive index as a function of transverse position, x, which is useful to reveal the molecular composition of the sample as well as provide an additional source of image contrast other than the reflectivity of the sample specimen 16. Finally, interferometric detection has the potential to allow elimination of high order multiple scattering from the confocal signal by coherence gating.

Figure 5A:
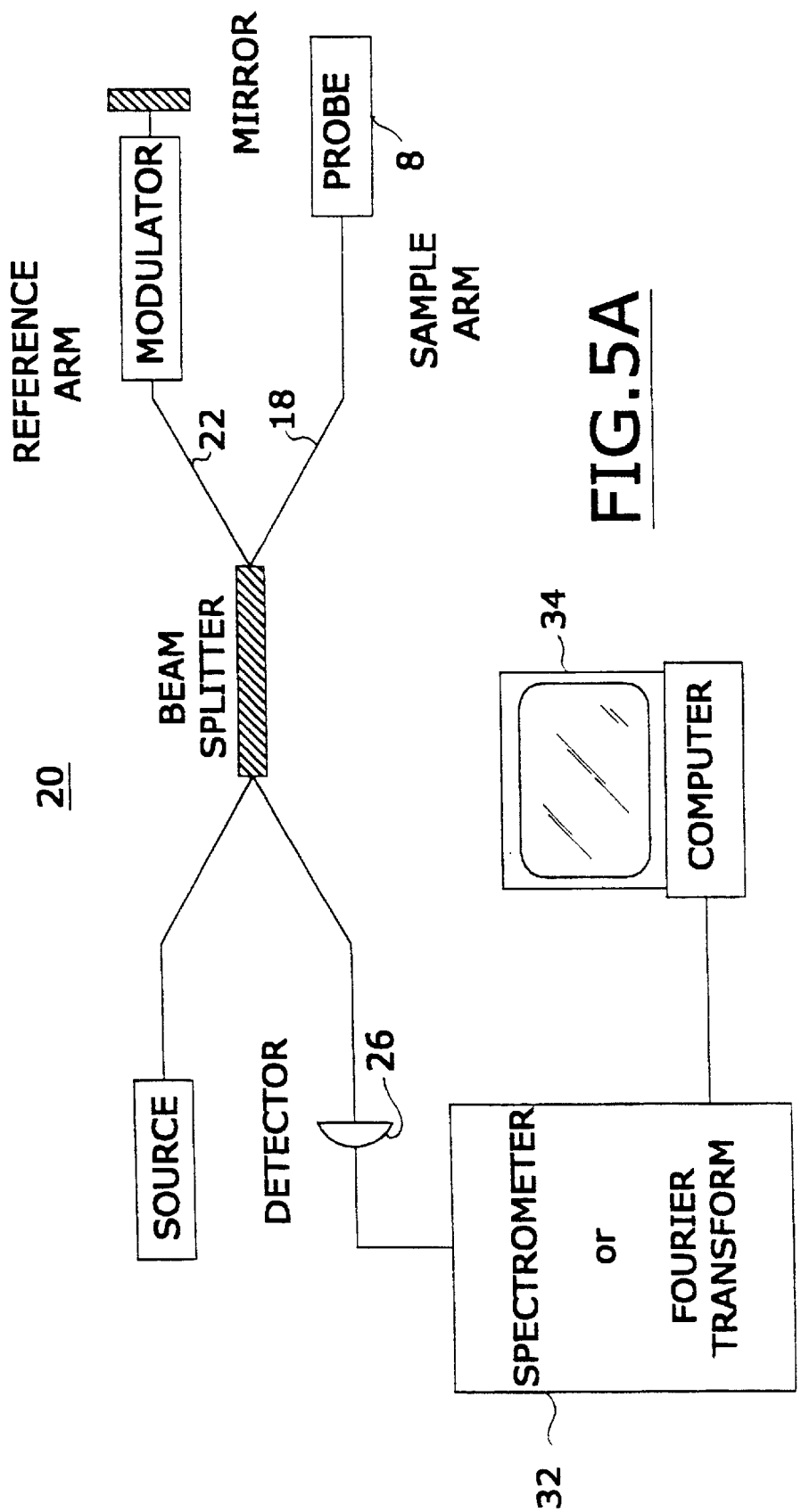

Consider finally image formation. The multi-spectral encoding of the transverse location, x, allows the performance of a one-dimensional raster scan. To obtain an image, a scan of another axis must be performed, which is usually slower. Methods of accomplishing this slow scanning of the y axis include moving the optical fiber 9 in the y direction (FIG. 5B), or rotating the entire probe 8 around the optical fiber axis either in a forward scanning configuration (FIG. 5C) or a side-firing configuration (FIG. 5D). Cross-sectional images may be created by scanning the optical fiber 9 or the objective lens 14 along the z axis (FIG. 6). Finally, a zoom mode may be created by scanning the optical fiber 9 (or another lens 32 between grating 12 and objective lens 14), in and out of the image plane of the objective lens (FIG. 7). Both linear motion along the y or z axis and rotation are easily accomplished in a compact probe by use of piezoelectric transducers. As shown in FIG. 5A, signals may be received by a computer 34 from spectroscopic detector 32 by a spectrometer (such as described in connection with FIG. 3) or Fourier transform (such as described connection with FIG. 4) representing an image of the a microscopic section of the sample, and the image displayed on a display coupled to the computer.

From the foregoing description, it will be apparent that the invention provides a confocal microscopy system which (a) is compact, optical fiber-based, capable of enabling confocal microscopy through a flexible catheter or endoscope; (b) is fast-scanning which takes place external to the probe; (c) allows phase information to be retrieved; and (d) provides a number of resolvable points proportional to the bandwidth of the source and the beam diameter on the grating. Variations and modifications in the herein described confocal microscopy system in accordance with the invention will undoubtedly suggest themselves to those skilled in the art. Accordingly, the foregoing description should be taken as illustrative and not in a limiting sense.

What is claimed is:

1. A confocal microscope system which comprises a probe movable into a body region of interest, said probe having means for illuminating said region with a confocal spectrum of light extending along one substantially transverse dimension, means for obtaining an image of the region of the specimen by moving said spectrum along another dimension and measuring the reflected confocal spectrum of light.

2. The system according to claim 1 wherein said probe is mounted on the end of a flexible, light-conducting member.

3. The system according to claim 2 wherein said member is an optical fiber.

4. The system according to claim 3 wherein said fiber is rotatable or translatable to move said probe in said another dimension.

5. The system according to claim 1 wherein said means for moving said spectrum comprises means for moving an image plane containing said spectrum optically or by physically moving said probe.

6. The system according to claim 5 wherein said probe is moved physically to scan said spectrum in said another dimension and said probe has means for optically moving said image plane to scan in still another direction, thereby enabling 3-D imaging.

7. The system according to claim 1 wherein said means for obtaining said image comprises heterodyne detection means.

8. The system according to claim 7 wherein said heterodyne detection means includes an interferometer.

9. The system according to claim 8 wherein said interferometer has a sample arm terminated by said probe, a reference arm terminated by a mirror, an output arm having a spectroscopic detector, an input arm having a source of polychromatic illumination, and a beam splitter for directing light from said source to said sample and reference arms and directing interfering light containing said reflected confocal spectrum into said output arm.

10. The system according to claim 9 wherein said reference arm includes means for modulating said reflected spectrum.

11. The system according to claim 10 wherein said modulating means comprising means for reciprocally oscillating said mirror or a modulator.

12. The system according to claim 11 wherein said modulator or reciprocal oscillation is at a certain frequency, and means for lock-in operation of said detector at said frequency.

13. The system according to claim 9 wherein said detector is a spectrometer.

14. The system according to claim 9 wherein said detector includes a cross-correlator or a Fourier transform spectrometer.

15. The system according to claim 1 wherein said probe comprises a grating and an objective which provides said confocal spectrum in an image plane of said objective.

16. The system according to claim 15 wherein said probe is sufficiently small size to be insertable into an organ internal of said body.

17. A system for confocally imaging tissue comprising:

a source for producing light;

means for producing a confocal spectrum of said light;

means for focusing said confocal spectrum in a direction into said tissue defining a first dimension and receiving returned light from said tissue, in which said confocal spectrum producing means is capable of providing a confocal spectrum which when focused by said focusing means extends along a second dimension in said tissue different from the first dimension; and means for detecting said returned light in accordance with a spectrum of said returned light to provide an image representing said tissue.

18. The system according to claim 17 further comprising means for scanning said confocal spectrum in at least one dimension with respect to said tissue.

19. The system according to claim 17 wherein at least said producing means and said focusing and receiving means are located is a probe capable of insertion in a body.

20. The system according to claim 17 further comprising an optical fiber which provides said light from said source to said producing means, and provides said returned light from said focusing and receiving means to said detecting means.

21. The system according to claim 17 wherein said producing means and focusing means are provided by more than one optical element.

22. The system according to claim 17 wherein said detecting means comprises at least a spectrometer.

23. The system according to claim 22 further comprising interferometric means for enabling said detecting means.

24. The system according to claim 17 wherein said light is polychromatic, said focusing means provides for focusing said confocal spectrum into said tissue along multiple positions in the tissue encoded in accordance with characteristics of the polychromatic light and said confocal spectrum producing means, and said detecting means spectroscopically detects said returned light to provide an image of a section of the tissue in accordance with the encoded positions of the confocal spectrum focused in the tissue.

25. The system according to claim 17 wherein said second dimension is substantially transverse with respect to said first dimension.

26. A method for confocally imaging tissue comprising the steps of:

providing a source of polychromatic light;

producing a confocal spectrum of said light with the aid of a diffractive element;

focusing said confocal spectrum into said tissue along multiple substantially transverse positions in the tissue encoded in accordance with characteristics of the polychromatic light and said diffractive element;

receiving returned light from the tissue; and spectroscopically detecting said returned light and producing an image of a section of the tissue in accordance with the encoded positions of the confocal spectrum focused in the tissue.

27. A system for imaging tissue comprising:

a diffractive element capable of providing illumination of one or more wavelengths along a first dimension; and a lens which focuses said illumination in a direction into said tissue along a second dimension different from said first dimension, and said lens receives returned illumination from said tissue representative of one or more locations in said tissue in accordance with said one or more wavelengths.

28. The system according to claim 27 further comprising a probe comprising at least said lens and said diffractive element.

29. The system according to claim 27 wherein said first dimension is substantially transverse with respect to said second dimension.

30. The system according to claim 27 wherein said lens focuses said illumination into one or more spots in the tissue at said one or more locations in accordance with said one or more wavelengths.

31. The system according to claim 27 further comprising means for scanning said tissue with said illumination focused by said lens.

32. The system according to claim 31 further comprising means for detecting said returned light to provide an image of said tissue representative of said region of said tissue.

* * * * *